United States Patent
Chen et al.

(10) Patent No.: US 10,514,339 B2
(45) Date of Patent: Dec. 24, 2019

(54) TEST STRIP ANALYSER HAVING FRAME WITH MOVABLE SUPPORT AND TEST STRIP CARRIER

(71) Applicant: HTC Corporation, Taoyuan (TW)

(72) Inventors: Chung-Jung Chen, Taoyuan (TW); Ming-Tien Lin, Taoyuan (TW)

(73) Assignee: HTC Corporation, Taoyuan (TW)

(*) Notice: Subject to any disclaimer, the term of this patent is extended or adjusted under 35 U.S.C. 154(b) by 364 days.

(21) Appl. No.: 15/250,944

(22) Filed: Aug. 30, 2016

(65) Prior Publication Data

US 2018/0059027 A1    Mar. 1, 2018

(51) Int. Cl.

| | | |
|---|---|---|
| *G01N 21/78* | (2006.01) | |
| *G01N 33/52* | (2006.01) | |
| *G01N 33/487* | (2006.01) | |
| *A61B 10/00* | (2006.01) | |
| *G01N 21/84* | (2006.01) | |
| *G01N 35/00* | (2006.01) | |
| *G01N 21/77* | (2006.01) | |

(52) U.S. Cl.
CPC ............ *G01N 21/78* (2013.01); *A61B 10/007* (2013.01); *G01N 21/8483* (2013.01); *G01N 33/4875* (2013.01); *G01N 33/48757* (2013.01); *G01N 33/52* (2013.01); *G01N 35/00029* (2013.01); *G01N 2021/7759* (2013.01); *G01N 2035/00039* (2013.01); *G01N 2035/00108* (2013.01); *G01N 2201/12* (2013.01)

(58) Field of Classification Search
None
See application file for complete search history.

(56) References Cited

U.S. PATENT DOCUMENTS

| | | | | |
|---|---|---|---|---|
| 5,184,359 | A * | 2/1993 | Tsukamura | ........ A61B 5/02241 |
| | | | | 4/314 |
| 5,460,968 | A * | 10/1995 | Yoshida | ........... G01N 35/00029 |
| | | | | 422/62 |
| 7,431,882 | B2 * | 10/2008 | Parker | .................. A61B 10/007 |
| | | | | 422/412 |
| 2002/0081233 | A1 * | 6/2002 | Lappe | ..................... B01L 3/502 |
| | | | | 422/82.05 |
| 2005/0081793 | A1 * | 4/2005 | Sannikka | ............. A61B 10/007 |
| | | | | 119/165 |

FOREIGN PATENT DOCUMENTS

WO    WO-2016054252 A1 *   4/2016   .......... B01L 3/50825

* cited by examiner

*Primary Examiner* — Christopher Adam Hixson
*Assistant Examiner* — Michelle Adams
(74) *Attorney, Agent, or Firm* — JCIPRNET (57) ABSTRACT

A test strip analyser is provided. The test strip analyser includes a frame, a test control module and an optical system. The test control module is disposed in the frame and includes a test strip carrier of a plurality of test strip carriers and a sample container of a plurality of sample containers. The test strip carrier is disposed on the frame and adapted to hold a test strip. The sample container is adapted to contain a sample. The optical system is disposed above the frame and the test control module and includes a light sensor and controller. The light sensor is configured to capture an image of the test strip. The controller is connected to the light sensor to control the light sensor, and the light sensor feedbacks the image to the controller. In addition, an analysing method using the same is also provided.

8 Claims, 5 Drawing Sheets

FIG. 7

TEST STRIP ANALYSER HAVING FRAME WITH MOVABLE SUPPORT AND TEST STRIP CARRIER

BACKGROUND OF THE INVENTION

1. Field of the Invention

The present invention generally relates to a test strip analyser and an analysing method using the same.

2. Description of Related Art

Analysis of blood samples or urine samples (urinalysis) is one of the most common methods of medical diagnosis. As various compounds pass through the sample, a wide range of disorders such as urinary tract infection, diabetes, kidney disease, etc. can be detected and assessed by analysing the sample. A test strip is a basic diagnostic tool used during analysis. A test strip consists of chemicals that react with the compounds in the sample. When a user dips a test strip into the sample, and then removes it from the sample, the test strip changes colors according to the compounds in the sample. Each compound has an optimized duration it takes to react with the test strip and change the color of the test strip. The result of the analysis is determined by comparing the color on the test strip with a color scale under naked eye examination.

However, it is often inconvenient for a user to dip a test strip into the sample and the process can be unsanitary. In addition, the optimized duration of reaction for each compound timed by the user can often be inaccurate. Furthermore, the test results can often be unreliable and biased by comparing the color on the test strip with a color scale under naked eye examination. Thus, there is the need for an accurate, convenient and sanitary test strip analyser for samples such as urine or blood.

SUMMARY OF THE INVENTION

Accordingly, the present invention is directed to a test strip analyser including a frame, a test control module and an optical system. The test control module is disposed in the frame and includes a test strip carrier of a plurality of test strip carriers and a sample container of a plurality of sample containers. The test strip carrier is disposed on the frame and adapted to hold a test strip. The sample container is adapted to contain a sample. The optical system is configured above the frame and the test control module, and includes a light sensor and a controller. The light sensor is configured to capture an image of the test strip. The controller is connected to the light sensor to control the light sensor, and the light sensor feedbacks the image to the controller.

The invention is also directed to a test control module configured in a test strip analyser. The test strip analyser includes a frame and an optical system. The frame includes a movable support, and the optical system includes a light sensor. The test control module includes a test strip carrier and a sample container. The test strip carrier is adapted to hold a test strip and is supported by the movable support. The sample container is adapted to contain a sample and is configured below the light sensor.

The invention is also directed to a sample analysing method of using a test strip analyser. The method includes collecting a sample in a sample container. Next, the sample container is placed in a frame of the test strip analyser. Next, a test strip carrier having a test strip is placed on a movable support of the frame. Next, the movable support is moved so that the test strip on the test strip carrier is moved to be in contact with the sample in the sample container. Next, an image of the test strip is captured with a light sensor and processing the image and analysing the sample with the controller.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Reference will now be made in detail to the present preferred embodiments of the invention, examples of which are illustrated in the accompanying drawings. Wherever possible, the same reference numbers are used in the drawings and the description to refer to the same or like parts.

Figure 1:
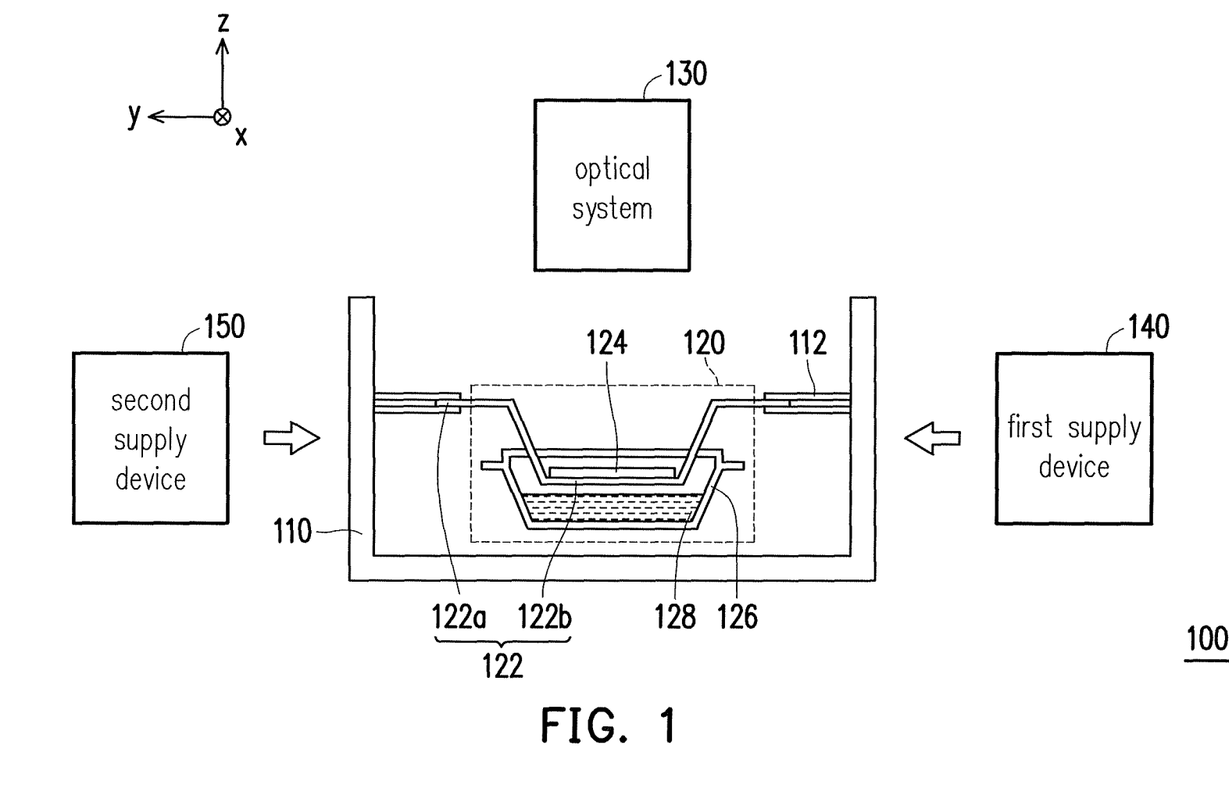
FIG. 1 is a schematic side view of a test strip analyser according to an embodiment of the invention.

FIG. 1 is a schematic side view of a test strip analyser according to an embodiment of the invention. Referring to FIG. 1, the test strip analyser 100 includes a frame 110, a test control module 120, an optical system 130, a first supply device 140 and a second supply device 150. The test control module 120 is disposed in the frame 110. The optical system 130 is configured above the frame 110 and the test control module 120. The first supply device 140 and the second supply device 150 are disposed adjacent to the frame 110.

In the embodiment, the test control module 120 includes a test strip carrier 122 and a sample container 126. The test strip carrier 122 is made of, for example, paper or plastic. However, the invention is not limited thereto, and the test strip carrier 122 may be made of any other suitable material. The test strip carrier 122 is disposed on the frame 110 and holds a test strip 124 for analysis. The test strip 124 reacts by, for example, changing colours, when dipped into a sample 128 such as urine. The sample may also be blood or any other type of physiological sample needed for analysis. The sample container 126 is adapted to contain the sample 128. The sample container 126 is made of, for example, paper or plastic or any other suitable material. The test strip carrier 122, the test strip 124 and the sample container 126 are disposable.

In the embodiment, the frame 110 of the test strip analyser 100 includes a movable support 112. The movable support 112 is slidably disposed on the frame 110, and supports the test strip carrier 122. The movable support 112 is able to move the test strip carrier 122 having the test strip 124 to be in contact with the sample 128 in the sample container 126, so that a user would not have to dip the test strip 124 in the sample 128 manually. The movable support 112 can slide vertically, horizontally, or diagonally on the frame 110 according to user requirements.

In the embodiment, the test strip carrier 122 includes a supporting portion 122a and a carrying portion 122b. The supporting portion 122a is supported by the movable support 112. Specifically, in the embodiment, the supporting portion 122a is inserted in the movable support 112 and the movable support 112 carries the supporting portion 122a. The supporting portion 122a is for example, clamped to the movable support 112. However, the invention is not limited thereto, and the supporting portion 122a can be supported or fixed to the movable support 112 in any other suitable method. The carrying portion 122b is for carrying the test strip 124. The supporting portion 122a and the carrying portion 122b are offset and spaced apart from each other in the direction the movable support 112 slides. In the embodiment, the supporting portion 122a and the carrying portion 122b are offset in the vertical direction, and are parallel to each other. That is to say, the supporting portion 122a and the carrying portion 122b are located on different planes (y-planes). As seen in FIG. 1, the carrying portion 122b is lower than the supporting portion 122a, and so when the movable support 112 slides down vertically, the carrying portion 122b with the test strip 124 also moves down into the sample 128. Thus, the test strip 124 is able to move down into the sample 128 accurately and conveniently through the movable support 112 and the test strip carrier 122. Thus, the user does not have to worry about spilling the sample 128 or getting the sample 128 on the hand of the user. In addition, the user does not have to worry about the test strip 124 not being fully immersed in the sample 128. In the embodiment, the movable support 112 is moved automatically. However, in other embodiments, the movable support 112 is moved manually. That is to say, the user can manually push or pull a mechanism to control the movable support 112 to move. Thus, even though the movable support 112 is moved manually, the user does not have to directly dip the test strip 124 into the sample 128.

Figure 2:
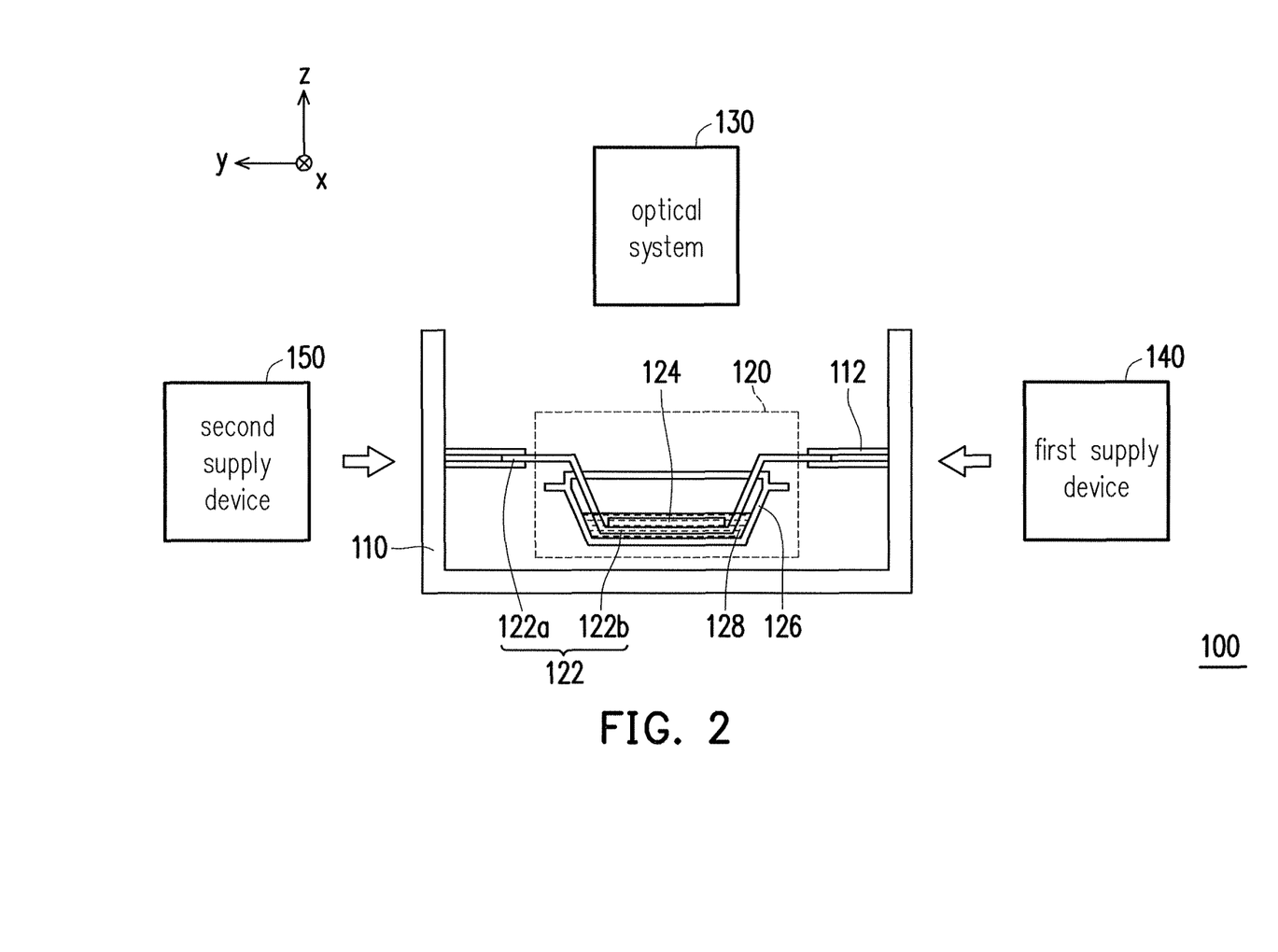
FIG. 2 is a schematic side view of the test strip analyser of FIG. 1 with a test strip in contact with a sample.

FIG. 2 is a schematic side view of the test strip analyser of FIG. 1 with a test strip in contact with a sample. Referring to FIG. 2, the movable support 112 has slided down vertically so that the test strip carrier 122 and the test strip 124 are in contact with the sample 128. Specifically, the test strip 124 along with part of the test strip carrier 122 is immersed in the sample 128. As seen in FIGS. 1 and 2, in the embodiment, the movable support 112 slides vertically. However, depending on the configuration of the frame 110, in other embodiments, the movable support can slide horizontally or diagonally.

Figure 3:
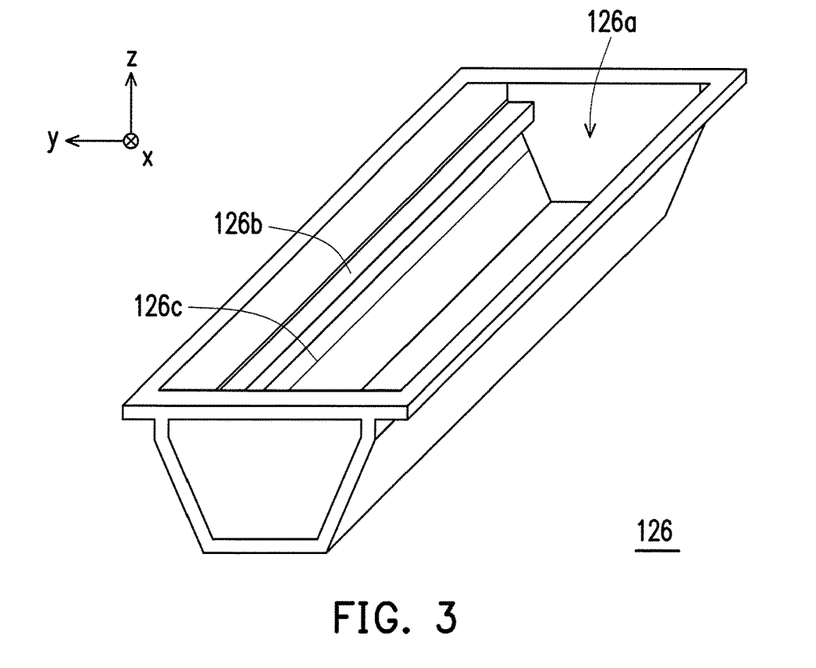
FIG. 3 is a schematic three dimensional view of a sample container of the test strip analyser of FIG. 1.

FIG. 3 is a schematic three dimensional view of a sample container of the test strip analyser of FIG. 1. Referring to FIG. 3, the sample container 126 includes an opening 126a and an absorbing element 126b. The sample container 126 as shown in FIG. 3 does not include the sample 128. The absorbing element 126b is disposed in the sample container 126 adjacent to the opening 126a. The absorbing element 126b is used to absorb an excess of sample 128 from the test strip 124. That is to say, if the test strip 124 drips off any of the liquid sample 128, the sample 128 may be absorbed by the absorbing element 126b. If the sample container 126 is tilted or is bumped around during the process of being moved, the sample 128 that is splashed or spilled may be absorbed by the absorbing element 126b. The absorbing element 126b can help in keeping the test strip analyser 100 sanitary and clean. The absorbing element 126b is made of, for example, sponge, cotton, paper, or fiber-based materials. However, the invention is not limited thereto, and the absorbing element 126b may be made of any other suitable material. The absorbing element 126b as shown in FIG. 3 is only on one side of the sample container 126. However, the absorbing element 126b can also be on all sides of the sample container 126 or on some of the sides of the sample container 126b according to user requirements.

In addition, an interior of each of the sample containers 126 includes a reference line 126c parallel to an edge of the sample container 126. The reference line 126c acts as a marker for the user so that the sample 128 collected in the sample container 126 does not exceed the reference line 126c. In keeping the amount of sample 128 collected in the sample container 126 below the reference line 126c, the cleanness of the test strip analyser 100 can also be maintained. That is to say, the risk of the sample 128 being spilled from the sample container 126 is reduced. The reference line 126c as shown in FIG. 3 is only on one side of the sample container 126. However, the reference line 126c can also be on all sides of the sample container 126 or on some of the sides of the sample container 126b according to user requirements. In the embodiment, the reference line 126c is engraved in the sample container 126. In other embodiments, the reference line 126c may be marked in any other suitable way.

Figure 4:
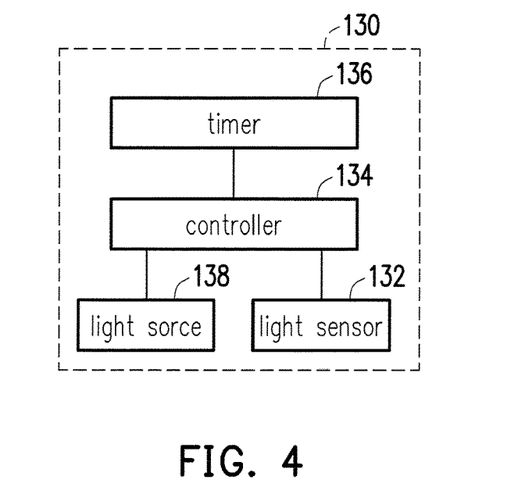
FIG. 4 is a block diagram of an optical system of the test strip analyser of FIG. 1.

FIG. 4 is a block diagram of an optical system of the test strip analyser of FIG. 1. The optical system 130 is configured above the frame 110 and the test control module 120. Specifically, the optical system 130 is disposed above the frame 110 and the test control module 120. The optical system 130 may be integrated with a housing (not shown) of the test strip analyser 100 or connected to frame 110 through any suitable method. The optical system 130 of the test strip analyser 100 includes a light sensor 132 and a controller 134. The light sensor 132 is above the test strip 124 and is configured to capture an image of the test strip 124. The light sensor 132 can be, for example, a camera, a photodiode, a charge-coupled device (CCD) image sensor or a complementary metal-oxide semiconductor (CMOS) image sensor. However, the invention is not limited thereto, and the light sensor 132 may be of various types according to user requirements.

In the embodiment, the controller 134 is connected to the light sensor 132 to control the light sensor 132, and the light sensor 132 feedbacks the image to the controller 134. The controller can be, for example, a processor or a computer, but the invention is not limited thereto. Furthermore, as mentioned above, the movable support 112 is moved automatically. Specifically, the movable support 112 is controlled by the controller 134 to move automatically.

In the embodiment, the optical system 130 further includes a light source 138 connected to and controlled by the controller 134. The light source 138 provides a light towards the test strip 124. The light source 138 can be, for example, incandescent lamps, fluorescent lamps or LEDs, and the light source 138 is always turned on during taking of the photos and is not needed to be controlled by users. However, the invention is not limited thereto, and the light source 138 may be of various types according to user requirements. The light source 138 can be turned on or off by the controller 134 as programmed by the user, or the light source 138 may be turned on or off manually.

In addition, a timer 136 is connected to the controller 134 and the light sensor 132, and the timer 136 feedbacks to the controller 134. The timer 136 times a duration the test strip 124 is in contact with the sample 128. Specifically, the timer times a duration of the test strip 124 being immersed in the sample 128. That is to say, the controller 134 controls the light source 138 to provide a light towards the test strip 124, the timer 136 to count a duration the test strip 124 is in contact with the sample 128, and the controller 134 controls the light sensor 132 to capture an image of the test strip 124. The light sensor 132 and the timer 136 feedbacks to the controller 134 for the controller 134 to process the image captured by the light sensor 132 and analyse the sample 128 in the sample container 126. The duration timed by the timer 136 depends on user requirements. That is to say, different types of samples 128 require different durations, which may be adjusted accordingly. Since the test strip analyser 100 includes the timer, the duration required for the test strip 124 to be immersed in the different samples can be precisely timed.

In the embodiment, the analysis is conducted by the controller 134 which provides more accuracy than analysis conducted by comparing the color on the test strip with a color scale under naked eye examination. During the analysis, algorithms are performed by the controller 134 to determine the presence of compounds in the sample 128 according to user requirements. The algorithms take into account the duration the test strip 124 is in contact with the sample 128 timed by the timer 136 and the image captured by the light sensor 132. The algorithms process the image captured and compare the color of the test strip 124 on the image to a color scale stored or programmed in the controller 134. The algorithm can calculate and output results such as whether a certain compound in the sample 128 is present or not, or provide a quantitative amount of a certain compound in the sample 128, or any other information according to user requirements. The analysis of the sample 128 can detect, for example, a urinary tract infection, diabetes, kidney disease, or other issues the user may want to detect. Since the timer times a precise duration, the timing is more accurate. In addition, since analysis performed by the controller is based on the image captured by the light sensor 132, the analysis is also more accurate.

Figure 5:
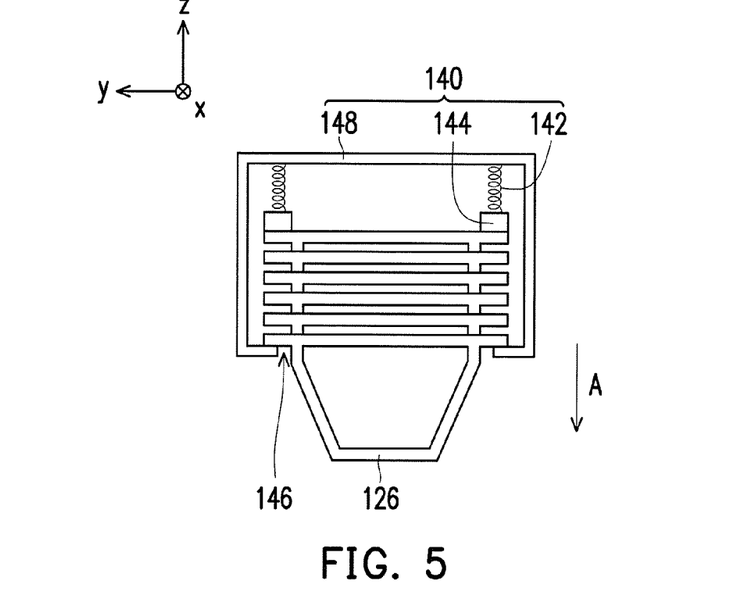
FIG. 5 is a schematic side view of a first supply device of the test strip analyser of FIG. 1.

FIG. 5 is a schematic side view of a first supply device of the test strip analyser of FIG. 1. Referring to FIG. 5, the first supply device 140 is adapted to contain a plurality of the sample containers 126. The first supply device 140 is adapted to hold the sample containers 126 stacked together. The first supply device 140 includes a plurality of mechanical components 144 disposed between a plurality of springs 142 and the top sample container 126 of the stack of sample containers 126. In addition, the first supply device 140 includes a housing 148 containing the stacked sample containers 126. The mechanical component 144 can be a stopper, a locking device or other various types according to user requirements. The mechanical components 144 act as an interface between the springs 142 and the top sample container 126. With the addition of the mechanical components 144, the force exerted by the springs 142 can be better transmitted to the top sample container 126. The first supply device 140 also includes an opening 146 exposing one of the sample containers 126. Specifically, the bottom sample container 126 of the stack of sample containers 126 is exposed by the opening 146. When a sample container 126 is removed from the first supply device 140 from the opening 146 in direction A, the plurality of springs 142 and the plurality of mechanical components 144 push the stack of sample containers 126 downward, in the direction A, to expose the next bottom sample container 126 of the stack of sample containers 126 through the opening 146. That is to say, the first supply device 140 acts as a dispenser for the sample containers 126. The process of dispensing the sample containers 126 may be automated in the test strip analyser 100. That is to say, the controller 134 controls the process of removing the sample container 126 form the first supply device 140 and placing it in the test control module 120. In some embodiments, the process is performed manually.

In the embodiment, the test strip analyser 100 further includes an indicator button (not shown). During the automated process, when the indicator button is pressed by the user, one of the sample containers 126 is placed in the test control module 120 through the controller 134. When the sample 128 is poured or disposed in the sample container 126, the controller 134 will detect the sample 128 in the sample container 126 through the optical system 130. Or, the controller 134 will detect the sample 128 in the sample container 126 through a level sensor (not shown), such as, for example, an optocoupler. Thus, the control 134 can detect how much of the sample 128 is disposed or poured in the sample container 126, to monitor the amount of the sample 128. Next, the test strip 124 is disposed in the sample 128. After the optical system 130 is done capturing or recording the image of the test strip 124, and the analysis is finished, the controller 134 controls the sample 128, the sample container 126, and the test strip carrier 122 to be removed. During the testing and analysing process, a light of the indicator button is on or flashing, and after testing and analysing is complete, the light of the indicator button is turned off. Different variations of how the light of the indicator button is controlled during the process may be adjusted according to user requirements. The automated process of removing or placing the sample 128, the sample container 126, and the test strip carrier 122 is controlled by the controller 134 and performed through any suitable mechanism known to one of ordinary skill in the art.

In addition, the first supply device 140 is disposed adjacent to the frame 110. Specifically, the first supply device 140 may be integrated in the housing (not shown) of the test strip analyser 100, or be connected to the frame 110 through any suitable method. The invention is not limited thereto.

Figure 6:
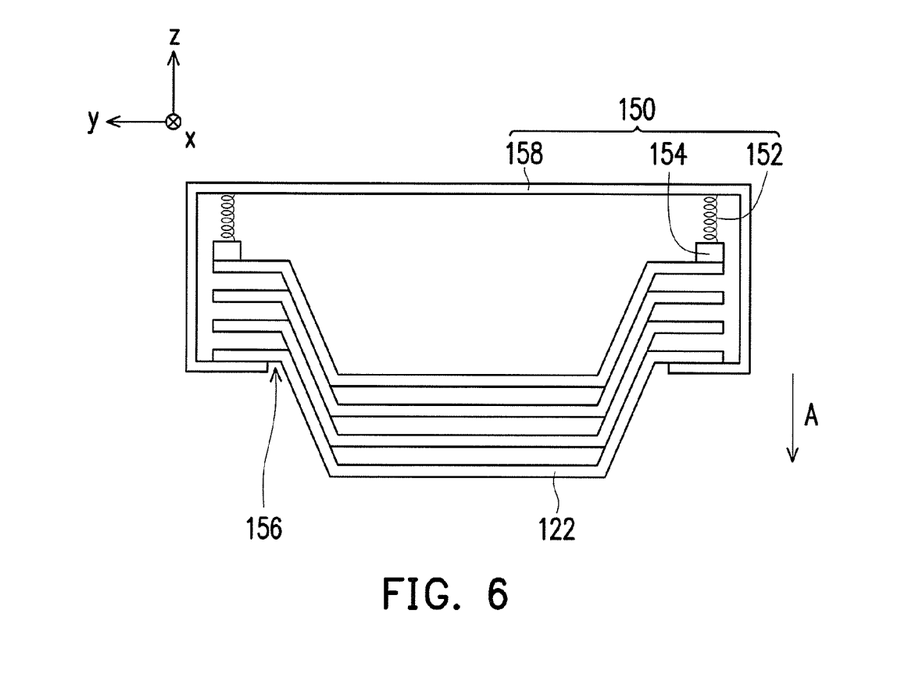
FIG. 6 is a schematic side view of a second supply device of the test strip analyser of FIG. 1.

FIG. 6 is a schematic side view of a second supply device of the test strip analyser of FIG. 1. In the embodiment, the second supply device 150 is adapted to contain the test strip carriers 122 as shown in FIG. 6. The second supply device 150 is adapted to hold the test strip carriers 122 stacked together. The second supply device 150 is similar to the first supply device and includes a plurality of mechanical components 154 disposed between a plurality of springs 152 and the top test strip carrier 122 of the stack of test strip carriers 122. The second supply device 150 also includes a housing 158 similar to the first supply device. The mechanical component 154 is similar to the mechanical component 144, and the same description will not be repeated herein. The second supply device 150 also includes an opening 156 exposing one of the test strip carriers 122. Specifically, the bottom test strip carrier 122 of the stack of test strip carriers 122 is exposed by the opening 156. When a test strip carrier 122 is removed from the second supply device 150 from the opening 156 in the direction A, the plurality of springs 152 and the plurality of mechanical components 154 push the stack of test strip carriers 122 downward, in direction A, to expose the next bottom test strip carrier 122 of the stack of test strip carriers 122 through the opening 156. Similar to the description of the first supply device 140, the process of dispensing the test strip carriers 122 with the second supply device 150 may be automatic or manual. The second supply device 150 is configured in the test strip analyser 100 similar to the first supply device 140. The same description will not be repeated herein.

Figure 7:
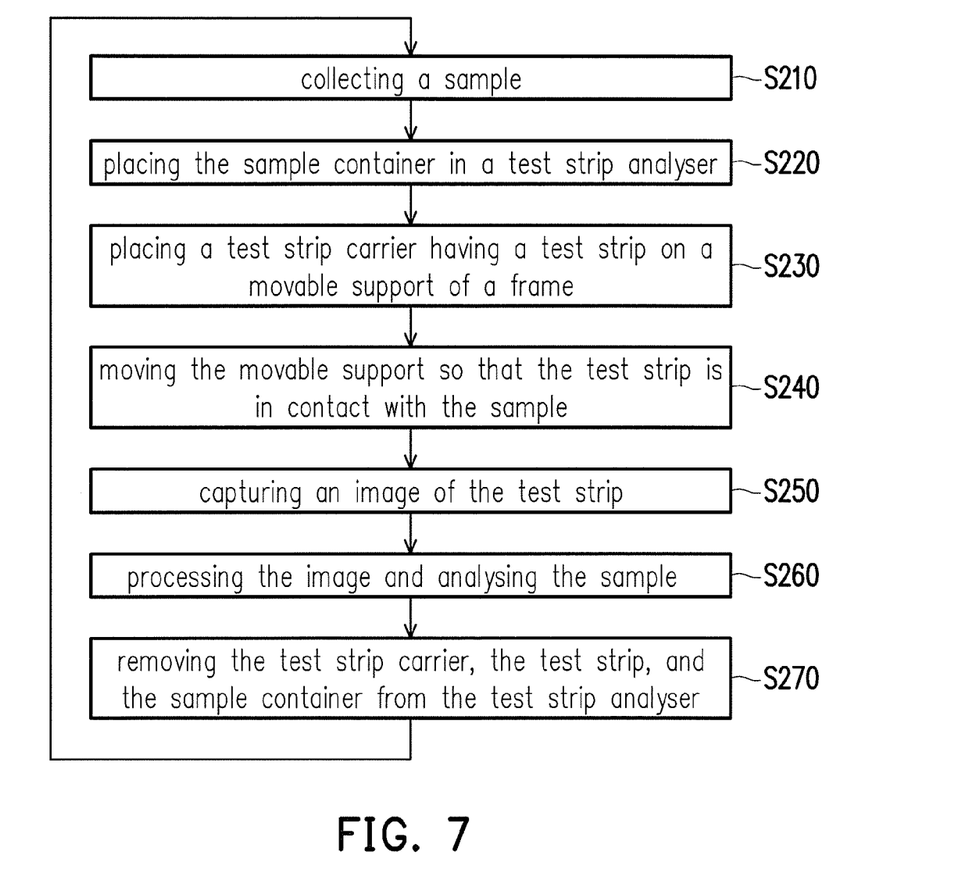
FIG. 7 is a flow diagram of a sample analysing method of using the test strip analyser of FIG. 1.

Referring to FIG. 7, a sample analysing method 200 of using a test strip analyser 100 and the steps thereof are respectively described as follows. In the sample analysing method, a sample 128 is collected in the sample container 126 (step S210). In the embodiment, the sample 128 is collected in a cup, and then poured into the sample container 126. However, the disclosure is not limited thereto, and the sample 128 may also be directly collected by the sample container 126. The sample 128 collected in the sample container 126 does not exceed the reference line 126c parallel to an edge of the sample container 126, so that the sanitary of the test strip analyser 100 can be maintained. Then, the sample container 126 is placed in the frame 110 of the test strip analyser 100 (step S220). The sample container 126 is placed in the test control module 120 between the movable support 112. Next, a test strip carrier 122 having a test strip 124 is placed on a movable support 112 of the frame 110 (step S230). Prior to step S230, a test strip 124 is placed on the test strip carrier 122. The position of the test strip 124 is on the test strip carrier 122 above the sample 128. Subsequently, the movable support 112 controlled by a controller 134 is moved down vertically so that the test strip 124 on the test strip carrier 122 is moved to be in contact with the sample 128 in the sample container 126 (step S240). However, depending on the configuration of the frame 110, in other embodiments, the movable support can slide horizontally or diagonally. When the test strip 124 is in contact with or immersed in the sample 128 in step S240, the controller 134 also controls the timer 136 to count a duration the test strip 124 is in contact with the sample 128. After the duration preset by the user is achieved, the timer feedbacks to the controller 134 to control the movable support 112 to move back upwards so that the test strip 124 is no longer in contact or immersed in the sample 128. Then, the controller 134 controls the light sensor 132 to capture an image of the test strip 124 (step S250). In step S250, the controller 134 can also control the light source 138 to provide a light towards the test strip 124. The light source 138 can be turned on or off by the controller 134 as programmed by the user, or the light source 138 may be turned on or off manually. Finally, the light sensor 132 feedbacks to the controller 134 for the controller 134 to process the image captured by the light sensor 132 and analyse the sample 128 in the sample container 126 (step S260). The analysis performed by the controller 134 may be referred to above, and the same description will not be repeated herein.

The sample analysing method 200 further includes removing the test strip carrier 122, the test strip 124, and the sample container 126 from the test strip analyser 100 (step S270). That is to say, the test strip carrier 122, the test strip 124, and the sample container 126 are disposable. Thus, in step S270, the test strip carrier 122, the test strip 124, and the sample container 126 are thrown away as trash and not reused. The step S270 may be performed manually, or may be automated within the test strip analyser 100. Next, the process may be repeated back to step S210. That is to say, another sample 128 is collected. Another sample container 126, test strip 124, and test strip carrier 122 are provided in the test strip analyser 100 in steps S210 to steps S230 either manually or automated. The steps S240 to S270 are then repeated again to analyse the new sample 128 that has been collected.

To sum up, the test strip analyser includes a movable support that moves the test strip carrier having the test strip to be in contact with the sample in the sample container. Therefore, a user would not have to dip the test strip in the sample manually. Thus, the test strip analyser provides a convenient and sanitary way for analysing samples such as urine or blood. Furthermore, the test strip analyser includes a controller that controls the timer to count a duration the test strip is in contact with the sample and controls the light sensor to capture an image of the test strip. The light sensor and the timer feedbacks to the controller for the controller to process the image captured by the light sensor and analyse the sample in the sample container. Therefore, the optimized duration of reaction for each compound is timed with a timer and can be more accurate, and the analysis is conducted by the controller which provides more accuracy than analysis conducted by comparing the color on the test strip with a color scale under naked eye examination. Thus, providing an accurate, reliable and unbiased analyser for analysing samples such as urine, blood or any other type of physiological sample needed for analysis.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A test strip analyser, comprising:
   a frame, comprising a movable support, the movable support being slidably disposed on a side portion of the frame to move in a first direction;
   a test control module disposed in the frame, comprising:
   a test strip carrier, disposed on the frame and adapted to hold a test strip, wherein the movable support supports the test strip carrier, the test strip carrier comprises a carrying portion and a supporting portion, wherein the carrying portion is disposed for holding the test strip, and the supporting portion is supported by the movable support and clamped to the movable support; and
   a sample container, adapted to contain a sample, the sample container including an opening and an absorbing element, the absorbing element protruding from an inner side of the sample container, and the absorbing element being adjacent to the opening, and the carrying portion with the test strip being movable down into the sample; and
   an optical system, configured above the frame and the test control module, the optical system comprising:
   a light sensor, configured to capture an image of the test strip; and
   a controller, connected to the light sensor to control the light sensor, and the light sensor feedbacks the image to the controller.

2. The test strip analyser as claimed in claim 1, wherein the carrying portion and the supporting portion are offset from each other in the first direction.

3. The test strip analyser as claimed in claim 1, further comprising:
   a first supply device, adapted to contain the sample container; and
   a second supply device, adapted to contain the test strip carrier.

4. The test strip analyser as claimed in claim 1, wherein an interior of the sample container comprises a reference line parallel to an edge of the sample container.

5. The test strip analyser as claimed in claim 1, wherein the optical system further comprises a timer connected to the controller, and the timer feedbacks to the controller.

6. The test strip analyser as claimed in claim 1, wherein the optical system further comprises a light source connected to and controlled by the controller.

7. The test strip analyser as claimed in claim 1, wherein a first supply device is adapted to hold a plurality of sample containers stacked together, and the first supply device comprises an opening exposing one of the plurality of sample containers.

8. The test strip analyser as claimed in claim 1, wherein a second supply device is adapted to hold a plurality of test strip carriers stacked together, and the second supply device comprises an opening exposing one of the plurality of test strip carriers.

* * * * *